United States Patent [19]

Saklad

[11] 4,226,846

[45] Oct. 7, 1980

[54] ALBUMIN MICROAGGREGATES FOR RADIOACTIVE SCANNING OF RETICULOENDOTHELIAL SYSTEMS

[75] Inventor: Eugene L. Saklad, Sudbury, Mass.

[73] Assignee: New England Nuclear Corporation, Boston, Mass.

[21] Appl. No.: 898,292

[22] Filed: Apr. 20, 1978

Related U.S. Application Data

[63] Continuation-in-part of Ser. No. 783,633, Apr. 1, 1977, Pat. No. 4,094,965.

[51] Int. Cl.² .................... A61K 29/00; A61K 43/00; C07G 7/00
[52] U.S. Cl. .................................. 424/1; 260/112 R; 260/122; 424/1.5; 424/9
[58] Field of Search ................ 424/1, 1.5; 260/112 R, 260/122

[56] References Cited

U.S. PATENT DOCUMENTS 3,720,761  3/1973  Hunter ..................................... 424/1
3,863,004  1/1975  Wolfangel ................................ 424/1
4,071,613  1/1978  Hunter ..................................... 424/1

OTHER PUBLICATIONS

Honda et al., J. of Nucl. Med., vol. 11, No. 10, 1970, pp. 580–585.

*Primary Examiner*—Benjamin R. Padgett
*Assistant Examiner*—Christine M. Nucker
*Attorney, Agent, or Firm*—Sewall P. Bronstein; George W. Neuner

[57] ABSTRACT

Microaggregates of a complex of (1) albumin, particularly human serum albumin and (2) a metal reducing agent, particularly a stannous reducing agent, preferably formed in the presence of a stabilizing ligand, which complex, when labelled with technetium-99m provides an excellent agent for imaging reticuloendothelial systems (RES), particularly the liver, spleen, and bone marrow; methods of making and using the same; a complex (physical or chemical) of technetium-99m with such microaggregates and methods of using such latter complex.

65 Claims, No Drawings
}

ALBUMIN MICROAGGREGATES FOR RADIOACTIVE SCANNING OF RETICULOENDOTHELIAL SYSTEMS

This application is a continuation-in-part of Ser. No. 783,673, filed April 1, 1977, now U.S. Pat. No. 4,094,965, and a continuation-in-part of Ser. No. 783,633 filed April 1, 1977.

BACKGROUND OF THE INVENTION

The present invention relates to an agent for radioactively imaging the reticuloendothelial system (RES) of vertebrates, especially primates, particularly the liver, spleen and bone marrow. Such agents are sometimes referred to as radioactive RES imaging agents. More particularly the invention relates to an RES agent comprising a $^{99m}$Tc-labelled microaggregated complex of a reducing metal and albumin, particularly human serum albumin (HSA), to the unlabelled microaggregated complex as such and in the form of a kit, to a method of making the same and to a method of using the same for RES imaging.

At one time the most common commercial RES imaging agent was a radio-colloid (particle size of 0.001–0.05 micrometers ($\mu$m)) of gold, stablized with gelatin, which, after injection into the blood stream, is removed by and collects in the RES to give a latent radioactive image thereof which can be converted into a visible image by the appropriate instrumentation.

This was displaced by $^{99m}$Tc-labelled sulfur colloid stabilized with gelatin, most of which has a particle size of $<0.1$–$1.0$ $\mu$m, and which is presently still the most widely used radioactive RES imaging agent despite its disadvantages of (a) requiring a relatively large number of components, (b) requiring boiling and neutralization steps for labelling by the user at the use situs, and (c) not being biodegradable. Most of the sulfur colloid RES agents on the market do give sharp clear simultaneous images of the liver and spleen.

A $^{99m}$Tc-labelled stannous hydroxide colloid has also been marketed as an RES agent but it has the disadvantage that it is difficult to prevent growth of the colloidal particles after labelling without the subsequent addition of stabilizers by the user at the use situs which make them unsatisfactory for RES imaging, i.e., they are not stable.

Another RES agent which has been marketed in small quantities is a $^{99m}$Tc-labelled stannous phytate complex which, it is believed, is converted to an insoluble colloid by calcium in the blood stream, from which it is then removed by the RES. However, with this agent, difficulty has been encountered in obtaining a clinically acceptable clear, sharp image of the spleen simultaneously with the normal healthy liver. Accordingly, the use thereof has not become widespread.

SUMMARY OF THE INVENTION

The present invention provides a highly stable biodegradable RES agent, which requires fewer components than the sulfur colloid RES agent, which does not require either a heating or neutralizing or any step by the user at the use situs other than addition of a $^{99m}$Tc pertechnetate solution but yet which gives clinically acceptable clear, sharp images of both the liver and spleen simultaneously, and a novel method of making and using the same.

This is achieved by microaggregating albumin anaerobically, preferably human serum albumin (HSA), in the presence of a reducing metal in ionic or physical or chemical complex form (hereinafter referred to simply as reducing metal), preferably a stannous chloride, stannous iodide, stannous fluoride or stannous bromide, to form microaggregated colloidal particles of the albumin and reducing metal which are either labelled with $^{99m}$Tc by admixture with a radioactive pertechnetate solution directly or which is freeze dried and sealed in a sterile pyrogen-free vial and stored until ready for use and is then labelled with $^{99m}$Tc by admixture with a radioactive pertechnetate solution at the use situs.

Preferably the microaggregation is also carried out in the presence of an additional ligand, preferably in a water soluble form, for stabilizng the reducing metal against precipitation before aggregation. Preferred ligands are the diphosphonates, preferably methylenediphosphonate, hydroxyethylenediphosphonate and aminoethanediphosphonate; the phosphates, such as the polyphosphates, e.g., the pyrophosphates; the aminocarboxylates, such as diethylenetriaminepentaacetate salts; the polyhydroxycarboxylates, such as glucoheptonate; and the polycarboxylates, such as the salts of carboxymethylcellulose. To date the diphosphonates have been found most preferable. However, other known physiologically and toxicologically compatible ligands for the particular reducing metal used are suitable. It has been found that the anion of certain useful reducing metal salts, such as stannous fluoride, itself, has a sufficiently high stability constant to preclude the necessity of an additional ligand. In such case, the fluoride anion itself functions as a stabilizing ligand for the stannous ion.

In accordance with the invention radioactive distribution by particle size of the microaggregated colloidal particles is as follows: at least 90–95, preferably at least 98, percent of the activity is associated with particles not more than 5 $\mu$m. For good splenic imaging simultaneously with the liver not more than 40–60, more preferably not more than 40–50, and still more preferably not more than 10 to 40, percent is associated with particles less than 0.1, preferably 0.2 $\mu$m. More preferably, for good simultaneous spleen and liver images, at least 40 to 60% and still more preferably more than 50% (the major portion) of the activity is associated with particles between 0.2 $\mu$m and 5, more preferably 3 $\mu$m. Good simultaneous spleen and liver images have been achieved where between 60 and 100% of the activity was associated with particles between 0.2 and 3 $\mu$m provided more than 90–98% was associated with those not greater than 5 $\mu$m. Good images of the liver with poorer simultaneous splenic images can be achieved where only 5 to 20% of the activity is associated with micro size particles between 0.2 and 5 $\mu$m, provided more than 90–98% are not greater than 5 $\mu$m, the remainder of the activity being associated predominantly with particles less than 0.2 $\mu$m.

Radioactivity distribution by particle size is obtained by passing a known aliquot of a diluted suspension of the $^{99m}$Tc-labelled microaggregated particles through a series of polycarbonate filter membranes (e.g., membranes sold under the name NUCLEPORE by Nuclepore Corporation assembled into NUCLEPORE filter housings according to the manufacturer's instructions and assembled in series into a stack of decreasing pore size (sometimes referred to as serial filtration technique)) and then measuring the radioactivity of the filtered particles within each filter housing and of the ultimate filtrate by conventional measurement techniques, dividing each amount by the total radioactivity and multiplying by 100 to obtain the percentage. The aliquot is diluted sufficiently to prevent or minimize occluding of the pores of the filters which will reduce their effective size and thereby result in an incorrect measurement. A preferred technique for diluting the aliquot will be described hereinafter. All particle sizes referred to herein are determined by this technique.

Although good liver imaging is achieved where virtually all of the particles are less than 0.2 $\mu$m, simultaneous splenic imaging is most frequently poor.

Accordingly, it is preferred to achieve a particle size distribution in which as many particles as possible fall between 0.1 or 0.2 $\mu$m and 5 $\mu$m, more preferably between 0.2 $\mu$m and 3 $\mu$m.

Broken down further, good simultaneous spleen and liver imaging results have been achieved with the following particle size distribution: not more than 4-10% greater than 5 $\mu$m, not more than 15% larger than 3 $\mu$m, at least 20% over 1 $\mu$m (mostly 1-3 $\mu$m), at least 80 to 90% over 0.2 $\mu$m, and preferably at least 40 to 50% between 0.4 and 3.0 $\mu$m, with not more than 5 to 10%, preferably no more than 5 to 8%, mobile (relatively low molecular weight solubles) on saline ITLC.

From less than 15 minutes to greater than 60 minutes after injection, excellent visualization of both spleen and liver are achieved with no significant non-target distribution at optimal acquisition for the target tissue. Marrow distribution, particularly in the vertebrae and pelvic area, can be imaged by acquisition for times beyond those which are optimal for liver and spleen, as is true of colloidal sulfur RES agents.

A solution of the albumin and reducing metal, preferably with an additional ligand in the solution, is heated at a controlled pH and temperature to form the microaggregates.

The aforesaid particle size distribution is achieved primarily by controlling the concentrations of the components, the pH and the heating conditions as described more fully hereinafter.

The reducing metal becomes bound to the albumin (it is believed that a physical or chemical complex is formed) which increases the selective binding efficiency of the Tc-99m to the denatured microaggregated albumin when the microaggregated albumin particles are subsequently labelled, to thereby provide increased RES uptake and clear RES imaging.

The function of the additional ligand is to increase the amount of the reducing metal which can be stabilized against hydrolysis (formation of insoluble hydroxides or hydrated oxides of the reducing metal) before microaggregation. In the course of denaturation of the albumin caused by heating, it is believed that conformational changes in the albumin expose reactive groups which enhance the affinity of the albumin for the reducing metal, thus binding substantially greater amounts of the reducing metal to and within the microaggregates than would otherwise be achieved in the absence of the additional ligand or as compared to reacting the reducing metal with the albumin after it is microaggregated. In any event, the additional ligand contributes substantially to the excellent radioactive imaging of the RES. However, as aforesaid, when the anion of the water soluble reducing metal salt has a sufficiently high stability constant to stabilize the reducing agent against hydrolysis, as in the case of the fluoride, the need for an additional ligand is obviated. In such cases the anion is in effect a stabilizing ligand for the reducing metal.

Where the microaggregates ($\mu$AA) are to be freeze dried for storage before use they are preferably admixed before freeze drying with a stabilizer solution of soluble undenatured (unaggregated) albumin (HSA) to aid in the dispersion (reconstitution) of the solid freeze dried particles in the pertechnetate solution when the latter is added thereto to label the microaggregates with Tc-99m for use thereof. In a preferred embodiment, the stabilizer solution also contains a non-ionic surfactant (preferably Pluronic F-68) to further aid in the dispersion of the solid freeze dried particles in the pertechnetate solution.

Also, buffers, such as sodium phosphate, are added (preferably with the unaggregated HSA and surfactant as part of the stabilizer solution) to achieve a pH sufficiently removed from the isoelectric point of the particles to stabilize the reconstituted preparation against particle growth when the pertechnetate solution is subsequently added to the freeze dried particles to form the $^{99m}$Tc-labelled albumin-Sn$^{++}$ microaggregates dispersed in saline or other pharmaceutically and pharmacologically acceptable carrier for injection into the patient. Therefore, it is advantageous to add such a buffered stabilizer solution in conjunction with labelling, even if the product is to be utilized without freeze drying.

Among the most preferred ligands are the diphosphonates; of these methylene diphosphonate (MDP) and hydroxyethylene diphosphonate (HEDP) are preferred, but any of the diphosphonates described in U.S. Pat. No. 4,032,625 and German Offenlegungsschrift No. 2,424,296 can be used.

Of the phosphates, pyrophosphate (preferably sodium pyrophosphate) is preferred. However, orthophosphate, the linear polyphosphates and organic phosphates, such as the inositolhexaphosphates may also be used.

Included among the aminocarboxylates which may be used are ethylenediaminetetraacetic acid (EDTA) salts and diethylenetriaminepentaacetic acid (DTPA) salts.

Although polyhydroxycarboxylates and polycarboxylates may function as weak ligands, they are not as suitable as those referred to above.

The stabilizing ligands which may be used are limited only by the ability to stabilize the reducing metal sufficiently against hydrolysis, and by toxicological considerations.

The most preferred albumin for human use is human serum albumin, although albumins from other species may be used for diagnostic applications for those respective species.

Although the stannous (Sn$^{++}$) ion is preferred as a reducing metal, others, such as the ferrous (Fe$^{++}$) ion and the monovalent copper ion (Cu$^+$) can also be used, but without as good results. All these reducing metals can exist in at least two cationic redox states of which a lower valence charge is required for reduction of pertechnetate in subsequent labelling.

To microaggregate, a solution of a mixture of the albumin, ligand and reducing metal is heated rapidly to a temperature between 70° C. and 100° C., more preferably 80°-100° C., and still more preferably between 85° C. and 99° C. Optimum results have been achieved with temperatures between 90° C. and 99° C. Higher temperatures can also be used provided the pressure is increased sufficiently to prevent substantial boiling of the reaction mass. Heating time may be between seconds and hours depending on the temperature and on the manner of heating. For example, heating by microwave energy or by radiofrequency heating or by induction heating requires only seconds whereas heating by immersion in boiling water or by passage through heating coils requires minutes. The maximum heating time is dictated by the fact that continued heating after formation of the microaggregates ($\mu$AA) may cause an increase in the particle size of the HSA-reducing metal complex beyond 5 $\mu$m and/or the production of soluble degradation products. Also boiling seems to increase particle size. The minimum heating time and temperature are dictated by the time and temperature required to achieve sufficient aggregation to obtain the micro particle size distribution desired as set forth above. The maximum heating time and temperature are dictated by the time and temperature beyond which too many of the particles become larger than 5 $\mu$m or degradation ensues. Using these guide lines, optimum heating temperature and time can easily be determined by routine testing of any given composition for any given manner of heating to provide the desired particle size distribution. Excellent results have been achieved with heating times of 3 to 10 minutes at heating temperatures of 90°–99° C. where heating was carried out in a hot water bath, with acceptable results being achieved with heating times of 2–5 minutes using such a bath and temperatures.

It is believed that the albumin becomes denatured during this heating step, i.e., denaturation occurs simultaneously with microaggregation.

The microaggregation by heating is carried out at a pH sufficiently removed from the isoelectric point of the albumin (at which there is a 0 or near 0 charge on the molecules) to give the aforesaid particle size distribution. In this respect commercial HSA is comprised of a mixture of albumins with a distribution of isoelectric points. Consequently, the isoelectric points of the mixture may vary from lot to lot. They have been reported to range from pH 4.8 to 5.5; however, the presence of charged compounds which tend to associate with the albumin may shift its apparent isoelectric point significantly. They are believed to exert this effect, either by imparting their own charge to the albumin or by neutralizing some positively or negatively charged groups on that protein.

The closer the pH is to the isoelectric point the larger the aggregate particles; thus at isoelectric pH macroaggregation or uncontrolled agglomeration occurs. As the pH is moved away from isoelectric pH toward the acid side and toward the alkaline side the particles become smaller and smaller. The optimum pH in the instant invention varies in accordance with the additional ligand which is used. It has been found that the desired particle size distribution of the microaggregates can be achieved over a range of pHs, which again depends upon the particular additional ligand used, the most desirable ligand being that which provides the desired particle size over the widest pH range, thereby giving the least sensitive and most easily reproducible system. It has also been found that increasing ionic strength, e.g., by adding a neutral salt such as NaCl, during aggregation will shift the pH at which the desired particle size distribution is obtained further from the isoelectric point. Preferably, aside from the additional ligand and the reducing salt, the only other materials present which will affect the ionic strength of the preaggregated bulk solution (the mixture which is subjected to aggregation) are the acid, e.g., HCl, or base, e.g., NaOH, used for pH adjustment. However, other materials which affect ionic strength may be present.

Although the desired particle size distribution can be achieved at a pH range on the acid side of the isoelectric pH and on the alkaline side, the latter is preferred since microaggregation on the acid side presents other difficulties.

On the acid side of the isoelectric point the pH may range from about 3.5 to 4.5 and on the alkaline side of the isoelectric point it may range from about 5.4 to 9.5, more preferably between 5.5 and 7.0 and still more preferably between 5.6 and 6.5, depending upon the additional ligand used, the isoelectric point of the particular albumin used and concentrations of components. However, where the apparent isoelectric point has been reduced by the presence of a charged compound as aforesaid, to below 4.5, the optimum pH may be as low as 4.5.

Under conditions explored with MDP, successful results have been achieved over a pH range of 5.4–6.6, more preferably 5.6–6.5 and optimum reproducible results have been achieved at a pH range of 5.7–6.35. Under conditions explored with pyrophosphate, optimum results have been achieved over a pH range of 5.9–6.1.

The optimum pH for any particular ligand in any particular concentration can be determined easily and routinely by aggregating at different pHs away from isoelectric point until the desired particle size distribution is achieved.

The reducing metal, e.g., stannous chloride, may be added to the albumin and ligand solution as a solid or it may be added as a solution.

The maximum amount of reducing metal is that beyond which precipitation thereof occurs before aggregation of the albumin. The minimum amount is that necessary to reduce and bind sufficient Tc-99m to the aggregated albumin to achieve clinically acceptable RES uptake. These amounts can be readily determined for particular admixtures by routine experiment. Very small amounts of reducing metal are effective for adequate reducing and binding of the Tc-99m to the aggregated albumin, e.g., less than an 8:1 molar ratio of stannous to albumin, but because it is easily oxidized, compositions using the minimum amount required may lose their effectiveness over a period of time after storage, handling or use. Accordingly, an excess over the minimum amount for adequate binding of the Tc-99m is used. As the amount of reducing metal is increased there appears to be a point for any given combination of starting compounds at which binding effectiveness of the Tc-99m to the albumin no longer increases either initially or as a function of time up to 24 hours or more after labelling.

Keeping this in mind the molecular weight ratio of reducing metal, particularly $Sn^{++}$, to albumin may vary over a wide range, i.e., from 8:1 to 80:1, preferably 30:1 to 50:1. It is preferred that the molecular weight ratio of $Sn^{++}$ to albumin not exceed 80:1. Excellent results have been achieved with molar ratios of $Sn^{++}$ to albumin of from about 30:1 to 50:1.

The minimum amount of additional ligand is that required to avoid the formation of any substantial amounts of the insoluble hydroxide or hydrated oxide of the reducing metal for any given composition by binding the reducing metal. The maximum amount is that beyond which it commences to compete substantially with the albumin for the Tc-99m when the microaggregates are admixed with the pertechnetate. Such ligands, when present in excess of that required to stabilize the reducing metal, particularly those with high affinity for Tc, may react with the Tc-99m to form complexes which seek bone, kidney, or other non-target tissues, thereby increasing non-target uptake at the expense of RES uptake and reducing the effectiveness of the microaggregates as RES agents. Accordingly, the amount of ligand should not be in substantial excess of that amount which is required to stabilize the reducing metal. The minimum and maximum amounts of ligand can be easily determined by routine testing for insoluble hydroxides before aggregation and by observing the effect on bone uptake, kidney uptake, urinary excretion, and other non-target distribution by the aggregated product. Furthermore, the greater the concentration of ligand the narrower may be the pH range over which the desired particle size distribution is achieved during aggregation. Accordingly, for optimum results it is desirable to use little more than the minimum amount of ligand necessary to maintain the reducing metal in solution before aggregation.

The concentration of additional ligand and the maximum and minimum amounts thereof also depends upon the ligand used, since some ligands, such as MDP, have a greater binding capacity (higher stability constant) and a lesser ionic strength than others. A ligand which provides the widest range of pH's over which the desired particle size distribution is achieved is the most desirable. The diphosphonates, particularly MDP and HEDP, fall in that category. The maximum and minimum amounts of ligand also depends on the particular pH at which the aggregation is carried out.

The optimal amount of additional ligand is too small to have any appreciable buffering effect or to appreciably reduce the target to non-target activity ratio even though the ligand may be one which is known to seek non-target tissues. It is interesting to note that the addition of ligand which is known to seek non-target tissues, enhances the target to non-target ratio.

Since it is the complexing moiety of the ligand which functions to bind the reducing metal, the concentration of ligand is best expressed as a molecular weight ratio of such moiety to reducing metal ion, e.g., $Sn^{++}$. This ratio is strongly dependent upon the choice of ligand. For one such as methylene diphosphonate, which has a fairly high stability constant, such ratio is preferably between 0.6:1 and 1.2:1; for one such as glucoheptonate, which has a fairly low stability constant, about 2½ times that ratio is preferred.

Using MDP and stannous chloride and a pH range of 5.4 to 6.6 successful results have been achieved with a ligand:$SnCl_2.2H_2O$ weight ratio of 0.5:1 to 1:1. If the pH is increased beyond this range the concentration of MDP may be increased to achieve the same biodistribution.

It is clear from the above that there is a functional interdependence between the choice and concentration of ligand and the optimal pH for obtaining particles of the proper size range during aggregation.

In a preferred embodiment of the invention the aggregation is carried out in the presence of a water soluble, pharmacologically and toxicologically acceptable surfactant of the same type which is preferably included in the stabilizer solution. Although good results have been achieved without the presence of a surfactant during aggregation it is preferred to use it as an additional safeguard since it is believed it may increase the reproducibility and stability of the aggregates with respect to particle size.

A wide variety of surfactants is suitable for use in the aggregation step and in the stabilizer solution. Preferably the surfactants are of the non-ionic type and are solids at room temperature. The useful surfactants are those which are non-toxic to blood components or tissues and preferably have a hydrophilic/lipophilic balance (HLB) of about 14 to about 40, more preferably about 27–30.5. When a surfactant is used in the aggregation step only a very small amount is usually used. Preferably, the surfactant in the preaggregated bulk, when one is used, is present in an amount of about 0.1% to about 10% of the albumin in such preaggregation bulk, more preferably about 2–8% by weight.

The surfactant dissolved in the stabilizer solution, as aforesaid, aids in the rapid dispersion (reconstitution) of the freeze dried albumin reducing metal aggregate in the pertechnetate solution when the latter solution is added thereto for administering to the patient. The amount of surfactant used in the stabilizer solution is usually much greater than the amount used in the aggregation step.

Preferably the surfactant in the stabilizer solution is present in an amount of about 0.2% to 20%, more preferably 1 to 10% of the lyophilized composition (solid basis).

Suitable surfactants for use during aggregation and in the stabilizer solution include Polysorbate 80, U.S.P., higher molecular weight polyethylene glycols such as Carbowaxes made by Union Carbide, and molecular combinations of polyoxyethylene and polyoxypropylene (ethylene oxide-propylene oxide block copolymers), e.g., the Pluronics, made by BASF Wyandotte. See also, McCutcheon's *Detergents and Emulsifiers,* North American Edition (1973) at pages 213–217, where many commercially available surfactants having HLB numbers between about 14 and 40 are listed. Most preferred are the Pluronics, particularly Pluronic F-68, which has a molecular weight of about 8350, an HLB No. of 29.0 and is a solid at room temperature.

Volume ratio of unaggregated albumin stabilizer solution (containing surfactants and buffers when they are used) to the aggregated human serum albumin (Aggregated Bulk) may vary over a wide range. Excellent results have been achieved with ratios of from 1:1 to 1:3, a ratio of 1:2 being preferred.

Based on the final lyophilized solid composition the ratio of soluble albumin to aggregated albumin may range from about 3:1 to 20:1, more preferably 5:1 to 15:1.

The buffering compound is added to the aggregated bulk either as part of the stabilizer solution, or when such solution is not used, as such, to maintain the pH at a level sufficiently removed from the isoelectric point to stabilize the composition against particle growth from compounding through lyophilization, or after labelling. A suitable pH range is between 7 and 9, preferably 8±0.5, for the reason set forth above. Any compatible pharmacologically and toxicologically acceptable buffer compound can be used, which does not compete significantly for the Tc-99m. Suitable buffers include mixtures of acids and salts of weak acids, such as the appropriate sodium salts of orthophosphoric acid.

In some instances, it may be desirable to add to the preaggregated bulk an electrolyte, such as alkali or alkaline earth metal soluble salts, e.g., NaCl, for adjustment of ionic strength.

The maximum amount of Tc-99m (pertechnetate) added to the albumin aggregates relative to the denatured and aggregated HSA is dictated by the fact that any substantial excess over that which becomes bound to the microaggregates has no beneficial effect and should be avoided for reasons having nothing to do with the invention, namely because the amount of radioactive material injected into the body should be kept to the minimum required. However, a slight excess over that which becomes bound to the microaggregates may be used. Based upon primate studies, up to 10% free pertechnetate would probably not impair clinical utility. The minimum amount is dictated by that amount required to give clinically acceptable images. The molecular weight ratio of Tc-99m to aggregated HSA (based on molecular weight of the HSA before aggregation) may be as great as 0.25 or greater.

The radioactive dosage of the Tc-99m labelled microaggregates of the invention may vary from 0.01 to 50 mCi (millicuries) per patient, but preferably is from 1 to 8.

Preferably, the volume of the pertechnetate solution added to the final bulk as such, or after freeze drying, may vary from 1–10, preferably 1–8, ml containing 1–300 or more, preferably 5–50, mCi per milligram of denatured albumin. The pertechnetate solution is usually the eluate from a conventional Tc-99m generator but it need not be.

Better binding of the reducing metal to the HSA and more homogeneous microaggregates are achieved with less oxidation of the reducing metal by admixing it and the additional ligand with the HSA before aggregation, with resulting improved RES imaging. It is believed that more intimate contact between the HSA and reducing metal is achieved because, as the HSA opens up during heating, the freshly exposed binding sites thereof react with the reducing metal before and during aggregation and the reducing metal becomes an intimate part of the microaggregate particles.

In any event, as aforesaid, it has been found that better results are achieved when the HSA is aggregated in the presence of the reducing metal. However, the presence of the reducing metal during aggregation presents problems which are not present when HSA is aggregated without the presence of the reducing metal and which are overcome by the presence of the ligand during aggregation, by control of pH and heating conditions during aggregation, and by maintaining anaerobic conditions throughout.

One such problem is to achieve the particle size distribution desired, another is the binding of the required amount of reducing metal to the denatured albumin; another is to avoid the formation of insoluble reducing metal hydroxides or hydrated oxides.

The water or other pharmaceutically acceptable carrier used to form the various solutions and in which microaggregation occurs is preferably apyrogenic distilled water which has been treated to reduce the oxygen contained therein.

Also, preferably all the steps of the process are carried out under anaerobic conditions, i.e., in the absence of oxygen, as for example under a nitrogen atmosphere.

In the preferred embodiment the mixture of stabilizer solution and denatured HSA-reducing metal microaggregates, containing the ligand, when one is used, are freeze-dried in conventional manner in sterile non-pyrogenic containers or vials which are sealed and marketed in the form of a kit which can be used at the use situs by adding the prescribed amount of radioactive pertechnetate to the vial.

With respect to the technique for determining the radioactive distribution of the microaggregates by particle size, an appropriate technique which has been used for diluting the aliquots of Tc-99m labelled microaggregates for passage through the filters arranged in series is by adding to the labelled microaggregates, i.e., the product resulting from the addition of the pertechnetate solution to the lyophilized aggregates, a dilution of the stabilizer solution in a volume ratio of 9 parts diluted stabilizer solution to 1 part of labelled aggregates. This ratio may vary over a wide range so long as the finally diluted aliquot does not unduly occlude the pores of the filter membranes. The stabilizer solution is diluted by adding a sufficient amount of saline solution thereto to dilute it to about the same solids concentration as that of the labelled product. The particle size distributions referred to herein were obtained by this technique. However, other techniques can be used.

Although the stabilizer solution is not required when the aggregated bulk is to be used without freeze drying (in such case the buffer can be added as such), it is preferred to add the stabilizer solution with buffer in any event to stabilize the particle size upon addition of the pertechnetate solution.

The process of the invention can be carried out as a batch process, a semi-continuous process or a continuous process using a relatively large heating surface to volume ratio.

Preferably the preaggregated bulk is filtered through a sterilizing membrane, e.g., an 0.22 μm sterilizing membrane, before aggregation and the stabilizer solution is filtered through a sterilizing filter before being added to the aggregated bulk.

Also preferably the final bulk (the mixture of the aggregated bulk and the stabilizer solution) is passed through a 3 μm filter to remove particles greater than 3 μm and is then dispensed into vials and lyophilized.

The aggregated bulk of the invention has a milky to hazy appearance depending on the conditions used in the aggregation step. At the lower pHs within the acceptable pH range it may be opaque. When the pH is increased toward the middle of the range it becomes more lightly milky with slight translucence, and as the pH continues to be increased within the range it becomes hazy.

DETAILED DESCRIPTION OF INVENTION (INCLUDING EXAMPLES)

Example 1

To 90 ml of mixing low oxygen water is added anaerobically the following: 0.6 ml Human Serum Albumin, 25% (25 g/100 ml) Salt Poor, U.S.P., the HSA weighing 0.15 grams, 3 ml sodium methylene diphosphonate (MDP) solution (0.5 grams methylene diphosphonic acid disolved in 100 ml 0.05 N sodium hydroxide), 11.15 ml 0.05 N sodium hydroxide for pH adjustment, 0.5 ml stannous chloride solution (4.2 grams stannous chloride dihydrate plus 1.5 ml 12 N hydrochloric acid diluted to 100 ml with low oxygen water), and 0.6 ml of a 1% aqueous solution of Pluronic F-68, an ethylene oxide-propylene oxide block copolymer nonionic surfactant.

The pH of the solution is 6.1. Aliquots of this solution filtered anaerobically through an 0.22 μm sterilizing membrane and heated for 3.5 minutes in a water bath at about 99° C. yield a milky suspension of microaggregates of the HSA and $Sn^{++}$.

To approximately 50 ml of low oxygen water is added anaerobically 5.7 grams disodium orthophosphate heptahydrate (buffer), 12 ml 25% HSA and 0.33 grams Pluronic F-68. After dissolving the solids, the stabilizer solution is diluted to 100 ml with low oxygen water and is passed through a sterilizing filter anaerobically.

3.3 ml of the above sterile stabilizing solution is anaerobically mixed with 6.7 ml of the sterile milky suspension of microaggregates. 1 ml aliquots of this formulation, which has a pH of 8 are dispensed aseptically into sterile non-pyrogenic 10 ml serum vials. The vials are freeze dried (lyophilized) in a conventional manner and under aseptic conditions to remove water. This provides solid microaggregates of the complex (chemical or physical) of denatured HSA and $Sn^{++}$. Each vial contains 1 milligram of microaggregated particles of complexed denatured and aggregated HSA, 10 milligrams of non-aggregated HSA, 0.1 milligrams of $SnCl_2$, 0.1 milligrams of MDP, 10 milligrams of phosphate buffer (expressed as disodium orthophosphate) and 1.14 milligrams of Pluronic F-68 surfactant.

The vials are sealed and stored until ready for use at which time the stannous microaggregated albumin contained therein is labelled with Tc-99m.

To prepare the Tc-99m labelled aggregates, five mls of fresh radioactive sodium pertechnate (about 100 mCi, although effective labelling is obtained from less than 1 mCi to greater than 300 mCi), removed as a sterile non-pyrogenic eluate from a sterile NEN Tc-99m generator in an 0.9% saline solution, is added aseptically to each vial; the vial is shaken to dissolve the soluble components and disperse the microaggregate particles in the saline solution thereby reconstituting the freeze-dried product and labelling the microaggregates.

Aseptic techniques and sterile, non-pyrogenic ingredients and containers are used at all steps.

| Activity distribution by particle size of the microaggregates revealed the following in one such preparation: | |
|---|---|
| Particle Size | % of Total |
| ≧5μm | 0.5 |
| 3–5μm | 1.5 |
| 0.2–3μm | 71.1 |
| <0.2μm | 26.9 |

1–5 mCi of this dispersion of Tc-99m labelled stannous microaggregates were injected into adult mice intravenously.

Fifteen minutes after intravenous injection the mice were sacrificed and the various organs, (liver, spleen, ect.) were counted by conventional gamma ray counting techniques to determine uptake of Tc-99m by each organ.

| Biodistribution in the mice 15 minutes after intravenous injection was as follows: | |
|---|---|
| Organ | % of Injected Dose per Organ |
| Liver | 87.8 |
| Spleen | 2.6 |
| Lungs | 0.5 |
| Carcass | 5.8 - includes bone marrow |
| Kidneys | 1.0 |
| G. I. Tract | 0.6 |
| Remainder | 1.6 |

1–5 mCi of similar preparations were injected intravenously into primates (baboons). Liver-spleen imaging was performed in conventional manner during the first 30 minutes after injection, using a gamma scintillation camera (Picker Dyna Camera II).

Simultaneous sharp, clear images of the liver and spleen were obtained with low background. Lung and soft tissue uptake was minimal. Excellent images of the bone marrow can also be obtained with appropriately longer exposure than that used for liver and spleen. These images were as good as those which can be obtained with sulfur colloid RES agent and would be clinically useful for accurate diagnostic purposes. Although biodistribution of radioactivity in mice can be relied on to predict in primates the selective uptake by the RES as a whole (liver, spleen and bone marrow) and contrast between uptake of the RES as a whole and uptake by the other organs, it does not correlate with the liver-spleen uptake ratio in primates, and hence with the quality of the splenic image individually and simultaneously with the liver image in primates. See Int. J. of Applied Radiation and Isotopes 1977, Vol. 28, pp 123–130. Accordingly, to predict this ratio and quality in humans it is necessary to image the RES of a primate such as the monkey or baboon.

The aforesaid biodistribution in mice and the RES radioactive images in primates shows that the radiolabelled stannous microaggregated albumin preparations of this example are excellent RES agents with excellent simultaneous spleen-liver definition.

Substantially the same results were achieved where the freeze-drying step was omitted; also good results may be achieved where the stannous microaggregated albumin is used directly without being freeze-dried and without addition of the stabilizing buffered HSA-Pluronic F-68 solution but with addition of sufficient buffer to achieve the same pH. However, when the microaggregates are freeze-dried without addition of such stabilizer solution it is difficult to redisperse them upon addition of the pertechnetate solution. Whether or not the microaggregates are freeze-dried, in the absence of the stabilization provided by the buffer, the particle size may increase in an uncontrolled fashion in pertechnetate-physiological saline.

In each of the following examples all the mixing and filtering and heating steps are carried out anaerobically, as in this example, and in each the 1 ml aliquots dispersed in the 10 ml sterile, nonpyrogenic vials, are subjected to the same steps as in Example 1, i.e., the aliquot may be freeze-dried and labelled, or it may be labelled without freeze-drying, and the labelled aliquot is analyzed for activity distribution by particle size as above. Biodistribution in mice and radioactive images of monkeys, when tested by these procedures, as indicated in each example, are performed in the same way as in Example 1.

Example 2

To 45 ml of mixing low oxygen water is added the following: 0.3 ml 25% HSA (75 milligrams HSA), 0.25 ml stannous chloride solution (as in Example 1), 0.3 ml 1% Pluronic F-68 Solution, 11.2 mg diethylenetriaminepentaacetic acid, and 1.65 ml 0.1 N sodium hydroxide. The pH of the solution is 6.54. Aliquots of this solution, filtered through an 0.22 μm sterilizing membrane and heated for 3.5 minutes at about 99° C., yield a light milky suspension of microaggregates of the denatured HSA and Sn++.

3.3 ml of a stabilizing solution compounded as in Example 1, is mixed anaerobically with 6.7 ml of the milky suspension. 1 ml aliquots of this formulation, which has a pH of 8, are dispensed into sterile, non-pyrogenic 10 ml serum vials as in Example 1. Test data on one such preparation, processed and labelled as described in Example 1 are as follows:

| Activity distribution by particle size: | |
|---|---|
| Particle Size | % of Total |
| ≧5μm | 1.1 |
| 3-5μm | 1.1 |
| 0.2-3μm | 68.4 |
| <0.2μm | 29.5 |

Example 3

To 45 ml of mixing low oxygen water is added the following: 0.3 ml 1% Pluronic F-68 solution, 0.3 ml 25% HSA (75 milligrams HSA), 0.25 ml stannous chloride solution (4.2 grams stannous chloride plus 3 ml 12 N hydrochloric acid, diluted to 100 ml with low oxygen water). 16.7 ml of this solution is mixed with 1 ml of a 1% aqueous solution of sodium pyrophosphate (10.2 milligrams $Na_4P_2O_7.10H_2O$) and 0.55 ml 0.025 N sodium hydroxide solution. The pH of the solution is 5.85. Aliquots of this solution, filtered through an 0.22 μm sterilizing membrane and heated for 3.5 minutes in boiling water give a milky suspension of microaggregates of denatured HSA.

To approximately 50 ml of low oxygen water is added 5.7 grams $Na_2HPO_4.7H_2O$, 12 ml 25% HSA, and 0.33 grams Pluronic F-68. After dissolving the solids this stabilizing solution is diluted to 100 ml with low oxygen water, and is passed through a sterilizing filter.

3.3 ml of the above stabilizing solution is mixed anaerobically with 6.7 ml of the milky suspension. 1 ml aliquots of this formulation, which has a pH of 8, are dispensed into 10 ml serum vials. Test data on one such preparation, processed and labelled as described after Example 1, are as follows:

| Activity distribution by particle size: | |
|---|---|
| Particle Size | % of Total |
| ≧5μm | 1.0 |
| 3-5μm | 1.0 |
| 0.2-3μm | 69.0 |
| <0.2μm | 29.0 |

Example 4

To 290 ml of mixing low oxygen water is added the following: 1 ml of an aqueous solution containing 0.2 grams Pluronic F-68 per 5 ml, 4 ml 25% HSA (1 gram HSA), 3 ml of a stannous chloride solution (4.64) grams stannous chloride dihydrate plus 2 ml 12 N hydrochloric acid, diluted to 100 ml with low oxygen water), 0.66 grams $Na_2HPO_4.7H_2O$ in 15 ml low oxygen water, and 4.04 ml 4 Molar sodium chloride solution. The pH of the solution is 6.5. After anaerobic filtration through an 0.22 μm sterilizing membrane, it is passed sequentially and continuously through two heat exchangers. This provides a semi-continuous method for aggregation which can be made fully continuous by use of metered and continuous flow of the compounding materials into a mixing chamber with continuous flow therefrom through the filter and heat exchangers with the exit from the heat exchangers being continuously metered into a mixing chamber into which the stabilizer solution is continuously metered and mixed with the resulting mixture being continuously passed through the 3 μm filter and dispensed into vials which may be continuously loaded into the freeze dryer. The first heat exchanger is heated by fluid maintained at about 99° C., and the second is cooled by fluid at ambient temperature, from which the aggregated products are collected anaerobically. The bulk average residence time in each heat exchanger ranges from 3 to 8 minutes, and yields a milky suspension of microaggregates of stannous denatured HSA.

To 10 ml sodium phosphate solution (9.5 grams $Na_2HPO_4.7H_2O$ per 100 ml) is added 2 ml 25% HSA (0.5 grams HSA), 6.25 ml Pluronic F-68 solution (4.0 grams per 100 ml), and water to a total volume of 35 ml of stabilizer solution. After mixing well, deoxygenation, and sterilizing filtration, 15 ml of the milky suspension is added, followed by thorough mixing once again.

1 ml aliquots of this formulation, which has a pH of 8, are dispensed into 10 ml serum vials. Test data of such preparation labelled as described in Example 1, are as follows:

| Activity distribution by particle size: | |
|---|---|
| Particle Size | % of Total |
| ≧3μm | 7 |
| 1-3μm | 16 |
| 0.2-1μm | 57 |
| <0.2μm | 18 |

| Biodistribution in mice, 15 minutes after intravenous administration: | |
|---|---|
| Organ | % of Injected Dose per Organ |
| Liver | 89.3 |
| Spleen | 1.1 |
| Lungs | 1.0 |
| Carcass | 7.7 |
| Kidneys | 0.5 |
| G. I. Tract | 0.2 |
| Remainder | 0.2 |

Example 5

To 45 ml of mixing low oxygen water is added the following: 0.3 ml 25% HSA (75 milligrams HSA), 0.25 ml stannous chloride solution (4.2 grams stannous chloride dihydrate plus 3 ml 12 N hydrochloric acid diluted to 100 ml with low oxygen water), 0.3 ml 1% Pluronic F-68 solution, and 3.7 ml 1% sodium pyrophosphate solution (prepared as in Example 3). The pH is 5.71. Aliquots of this preaggregation bulk solution, filtered through an 0.22 μm sterilizing membrane and subjected to sufficient microwave heating, e.g., 20 seconds, give a milky suspension of microaggregates of stannous denatured HSA.

This milky suspension is formulated with an HSA-sodium phosphate-Pluronic F-68 stabilizing solution to give a pH8 formulation, after which it is dispensed into vials and labelled with 7 ml $^{99m}$Tc-sodium pertechnetate all as in Example 3. The following results were obtained on one such preparation:

| Activity distribution by particle size: | |
|---|---|
| Particle Size | % of Total |
| $\geq 5\mu m$ | 2.1 |
| 3–5$\mu m$ | 3.1 |
| 0.2–3$\mu m$ | 84.0 |
| <0.2$\mu m$ | 10.8 |

| Biodistribution in mice 15 minutes after intravenous administration: | |
|---|---|
| Organ | % Injected Dose per Organ |
| Liver | 85.9 |
| Spleen | 4.3 |
| Lungs | 0.5 |
| Carcass | 5.3 |
| Kidneys | 1.0 |
| G. I. Tract | 0.7 |
| Remainder | 2.3 |

Examples 6 and 7

To 417 ml of mixing low oxygen water are added the following: 16.3 ml (0.75 grams) of purified HSA (delipidized by acidification and activated charcoal, as described in U.S. Pat. No. 4,094,965, followed by ultrafiltration, to give an albumin concentration of 4.6%), 2.5 ml stannous chloride solution (4.2 grams stannous chloride dihydrate plus 3 ml 12 N hydrochloric acid diluted to 100 ml with low oxygen water) and 3 ml 1% Pluronic F-68 solution. The resulting solution is mixed well with 25.6 ml of a 1% aqueous solution of sodium pyrophosphate (prepared as in Example 3) and 34.2 ml of 0.025 N sodium hydroxide. 150 ml of the resulting solution is filtered through an 0.22 $\mu m$ sterilizing membrane. This filtered pre-aggregation bulk, having a pH of 5.62, is reserved for Example 6.

An additional 3.4 ml 0.025 N sodium hydroxide is added to the remaining solution, while maintaining agitation. The pH is 6.11. Filtration is performed as above. This pre-aggregation bulk is reserved for Example 7.

Aliquots of both pre-aggregation bulks are heated for 3.5 minutes in a hot water bath at 99° C. to form microaggregates.

| Appearance | Example 6 | Example 7 |
|---|---|---|
| milky | X | |
| hazy | | X |

Formulated with stabilizing solution (pH of stabilized formulation 8) dispensed into vials and labelled with 5 ml $^{99m}$Tc-sodium pertechnetate, all as in Example 3, the following results were obtained:

| Activity distribution by particle size: | | |
|---|---|---|
| | % of Total | |
| Particle Size | Example 6 | Example 7 |
| $\geq 5\mu m$ | 1.9 | 0.7 |
| 3–5$\mu m$ | 2.8 | 1.3 |
| 1–3$\mu m$ | 32.7 | 1.3 |
| 0.2–1$\mu m$ | 50.5 | 4.6 |
| <0.2$\mu m$ | 12.2 | 92.1 |

| Biodistribution in mice 15 minutes after intravenous administration: | | |
|---|---|---|
| | % of Injected Dose per Organ | |
| Organ | Example 6 | Example 7 |
| Liver | 86.0 | 88.3 |
| Spleen | 3.3 | 2.2 |
| Lungs | 0.8 | 0.6 |
| Carcass | 6.2 | 7.3 |
| Kidneys | 1.0 | 0.7 |
| G. I. Tract | 1.0 | 0.3 |
| Remainder | 1.7 | 0.6 |

| Imaging in Monkeys: | Quality of Image | |
|---|---|---|
| Organ | Example 6 | Example 7 |
| Liver | Good | Good |
| Spleen | Good | Poor |
| Bone Marrow | Good | Good |

Deterioration in the quality of splenic imaging resulting from a sharp reduction in particle size caused by increasing the pH in Example 7 is evident from the correlation in Examples 6 and 7 between activity distribution by particle size (also reflected in appearance of aggregated bulks) and image quality in healthy primates.

Example 8

To 45 ml of mixing low oxygen water is added the following: 0.3 ml 25% HSA (75 milligrams HSA), 1.5 ml hydroxyethylenediphosphonate (HEDP) solution (an aqueous solution containing 0.21 grams HEDP in 30 ml), 0.25 ml stannous chloride solution (4.2 grams stannous chloride dihydrate plus 3 ml 6.15 N hydrochloric acid diluted to 100 ml with low oxygen water), 0.3 ml 1% Pluronic F-68 solution and 5.42 ml 0.05 N sodium hydroxide solution. The pH of the solution is 5.90. Aliquots of this preaggregation bulk solution, filtered through an 0.22 $\mu m$ sterilizing membrane and heated for 3.5 minutes in a hot water bath at 99° C., form a milky suspension of microaggregates.

Formulated with stabilizing solution (pH of formulation is 8), dispensed into vials and labelled with 5 ml $^{99m}$Tc-sodium pertechnetate, all as in Example 3, the following results were obtained:

| Activity distribution by particle size: | |
|---|---|
| Particle Size | % of Total |
| $\geq 3\mu m$ | 8.9 |
| 1.3$\mu m$ | 2.1 |
| 0.2–1$\mu m$ | 61.2 |
| <0.2$\mu m$ | 27.8 |

| Biodistribution in mice 15 minutes after intravenous administration: | |
|---|---|
| Organ | % Injected Dose per Organ |
| Liver | 92.8 |
| Spleen | 2.6 |
| Lungs | 0.4 |
| Carcass | 5.1 |
| Kidneys | 0.5 |
| G. I. Tract | 0.5 |
| Remainder | 2.3 |

The lyophilized stannous microaggregated albumin of the instant invention has a very long shelf life of at least one year at ambient temperatures (when protected from light). It is also stable for at least 24 hours after labelling although it is preferred that it be used within 8 hours after labelling when stored under refrigeration, for patient safety, because it contains no preservative.

$^{99m}$Tc-labelled biodegradable stannous-macroaggregates (greater than 5 μm) of HSA macroaggregated at or near the isolectric point of the HSA at which the particles have a 0 or near 0 charge (achieved by aggregating at the isolectric pH of about 4.8–5.5 and at a relatively high ion concentration) have been used commercially for radioactively imaging the lungs. They are also described in the patent literature. See U.S. Pat. Nos. 3,987,157; 3,863,004 and 3,872,226. However such agents are not suitable as RES agents since these larger size particles are removed from the blood stream by the lungs before they reach the liver, spleen and bone marrow. See also U.S. Pat. No. 4,024,233 and United States Pharmacopia XIX page 488.

An RES scanning kit of tin-containing Tc-99m-labelled minimicrospheres (mean diameter of 1 μm and 98% by weight less than 3 μm) of HSA maintained at a pH of 2.4 with a glycine-HCl buffer and said to be offered by 3M, is reported in Journal of Nuclear Medicine Vol. 16, No. 6, 1975, pp. 543. It is believed that these minimicrospheres are precipitated from a liquid HSA emulsion in an oil bath. It is not know at what point the tin is added. See also U.S. Pat. No. 3,937,668 and Int. J. of App. Rad. and Isotopes, 1970, Vol. 21, pp 155–167.

Also, it has been suggested in the literature to ultrasonically disintegrate radioiodinated and $^{99m}$Tc labelled macroaggregates of HSA to micro-size particles. (J.N.M. Vol. 13, 1972 pp 260–65; J.N.M. Abstract, Vol. 12, No. 6, 1971, pp 373; J.N.M. Abstract Vol. 10, No. 6, pp 453–4; Int. J. of Applied Radiation and Isotopes, 1975 Vol. 26, pp 31–32). However, there is no mention in these reports of the presence of a reducing metal during aggregation or a ligand therefor, and such products require a disintegrating step.

There is also reported in J.N.M. Vol. 12, No. 6, article commencing on pp 372 and ending on pp 373, Tc-99m and $^{131}$I labelled microaggregates of albumin but there is no mention of the presence of any reducing metal and ligand therefor and no teaching of how the microaggregates are formed.

In J.N.M. Vol. 10, No. 6, 1969 pp 454, there is described methods of labelling macro and microaggregates of serum albumin using ferric ions and ascorbic acid with no teaching of how the microaggregates are formed and with no mention of the presence of a reducing metal and ligand therefor.

In J.N.M. Vol. 9, No. 9, 1968 pp 482–5, a method of making microaggregates of HSA is described followed by radioiodinating them. There is no mention of a reducing metal and ligand therefor. In J.N.M., Vol. 11, No. 6, 1970, pp 387 there is described a method of preparing Tc-99m labelled microaggregates of albumin, particle size about 0.5 μm, in which the microaggregates are apparently formed from Tc-99m labelled unaggregated albumin (the unaggregated albumin was labelled with Tc-99m utilizing ferric chloride, ascorbic acid and acetate buffer); there is no mention of the presence of a reducing metal and ligand therefor.

In J.N.M. Vol. 12, No. 6, 1971 pp. 467–8 there is described a Tc-99m-labelled stannous hydroxide colloidal suspension used in liver imaging, but no mention of HSA or a stabilizing ligand in the preparation so described.

J.N.M. Vol. 11, No. 10 pp 580–85, 1970 describes microaggregation of HSA followed by labelling with technetium prereduced with ferric chloride and ascorbic acid. There is no mention of the presence of a reducing metal or ligand therefor during aggregation.

The following literature references describe iodinated HSA aggregates: Br. J. Exp. Path. Vol. 38, 1957, pp 35–48; Report of Scientific Exhibit entitled "Colloidal Radioalbumin Aggregates For Organ Scanning" 10th Annual Meeting, Nuclear Medicine Society, Montreal, Canada, June 26–29, 1963; J.N.M., Vol. 5, pp. 259–275, 1964; J. Lab. & Clin. Med., Vol. 51, No. 2, pp. 230–39, 1958; "Dynamic Clinical Studies With Radioisotopes" USAEC Division of Tech. Info., pp 285–317, June 1964; Invest, Radiol. Vol. 1, 1966, pp. 295–300; Report of G. V. Taplan et al, entitled "Preparation of Colloidal Suspensions of Human Serum Albumin I$^{131}$ For Estimating Liver Blood Flow and Reticulo-endothelial System Functions in Man," UCLA Report No. 481 Biology and Medicine, June 23, 1961, University of California, Los Angeles School of Medicine.

U.S. Pat. No. 4,054,645 describes the use of a stannous fluoride reducing agent with a number of different target seeking ligands, one of which is albumin, but there is no teaching of microaggregating albumin in the presence of a stannous salt and an additional non-target-seeking ligand.

U.S. Pat. No. 4,057,615 describes the use of a reducing agent complex with various target-seeking excipients (an improperly chosen term for target seeking ligands) wherein the association constant of the reducing agent anion for technetium is less than that of the excipient. There is no teaching of microaggregating in the presence of a reducing metal and non-target seeking ligand.

Although some of the aforesaid literature references refer to Tc-99m-labelled microaggregates of albumin as radioactive imaging agents, there is no such agent presently on the market for RES imaging, and colloidal sulfur continues to be the major RES agent on the market despite its disadvantages and even though Tc-99m labelled macroaggregates have become a major factor in the lung imaging market.

I claim:

1. A composition for labelling with Tc-99m for radioactive imaging comprising microaggregates of albumin and a reducing metal.

2. A composition according to claim 1, said composition also comprising an additional stabilizing ligand for said reducing metal.

3. A composition for labelling with Tc-99m for radioactive imaging comprising microaggregates of albumin and a reducing metal, said composition also comprising an additional stabilizing ligand for said reducing metal selected from the group consisting of a phosphonate, a phosphate, an aminocarboxylate, a polyhydroxycarboxylate and a polycarboxylate.

4. A composition according to claim 3, said reducing metal being $Sn^{++}$ and said ligand being a diphosphonate.

5. A composition according to claim 2, at least 90% of said microaggregates being not greater than 5 μm in particle size.

6. A composition according to claim 5, at least 40% of said microaggregates being between 0.2 and 5 μm in particle size.

7. A composition according to claim 5, at least 40% of said microaggregates being between 0.2 and 3 μm.

8. A composition according to claim 7, said reducing metal being stannous and at least the major portion of said microaggregates being between 0.2 and 3 μm in particle size.

9. A composition according to claim 5, no more than 50% of said microaggregates being less than 0.2 μm in particle size.

10. A composition according to claim 2, said albumin being human serum albumin and said reducing metal being stannous.

11. A composition according to claim 10 wherein said composition is stabilized with undenatured albumin and a buffer.

12. A composition according to claim 11 also containing a non-ionic surfactant.

13. A composition according to claim 10, microaggregated at a pH between 4.5 and 9.5 but on the alkaline side of the apparent isoelectric point of said albumin.

14. A composition according to claim 13, said pH being between 5.4 and 7.0.

15. A composition according to claim 10, said composition being in the form of a freeze-dried solid.

16. A composition according to claim 1, at least 90% of said microaggregates being not greater than 5 μm in particle size.

17. A composition for labelling with Tc-99m for radioactive imaging comprising microaggregates of albumin and a reducing metal, at least 90% of said microaggregates being not greater than 5 μm in particle size, and at least 40% of said microaggregates being between 0.2 and 5 μm in particle size.

18. A composition according to claim 17, no more than 50% of said microaggregates being less than 0.2 μm in particle size.

19. A composition according to claim 1, said albumin being human serum albumin, said reducing metal being stannous, said microaggregates being microaggregated at a pH of 3.5–9.5, said composition being stabilized with undenatured human serum albumin and a buffer, and said stabilized composition being freeze-dried.

20. A radioactive imaging agent comprising Tc-99m labelled microaggregates of albumin and a reducing metal, wherein at least 90% of said microaggregates have a particle size not greater than 5 μm and at least 40% of said microaggregates are between 0.2 and 5 μm.

21. An agent according to claim 20 also comprising a stabilizing ligand for said reducing metal.

22. A radioactive imaging agent comprising Tc-99m labelled microaggregates of human serum albumin and a stannous reducing metal, said agent also comprising a stabilizing ligand for said reducing metal selected from the group consisting of phosphonates, phosphates, aminocarboxylates, polyhydroxycarboxylates and polycarboxylates.

23. A radioactive imaging agent comprising Tc-99m labelled microaggregates of albumin and a reducing metal, said agent also comprising a diphosphonate stabilizing ligand for said reducing metal.

24. An agent according to claim 23, said ligand being hydroxyethylene diphosphonate.

25. An agent according to claim 23, said ligand being methylene diphosphonate.

26. An agent according to claim 22, not substantially more than 50% of said microaggregates being less than 0.2 μm.

27. An agent according to claim 21, at least 40% of said microaggregates being between 0.2 and 3 μm.

28. An agent according to claim 21, the major portion of said microaggregates being between 0.2 and 3.0 μm.

29. An agent according to claim 21, admixed with non-aggregated albumin, buffer and surfactant.

30. An agent according to claim 20, said albumin being human serum albumin, said reducing metal being stannous, at least 90% of said microaggregates having a particle size no greater than 5 μm and not substantially more than 50% of said microaggregates being less than 0.2 μm.

31. A radioactive imaging agent comprising Tc-99m labelled microaggregates of human serum albumin and a stannous reducing metal, at least 90% of said microaggregates having a particle size no greater than 5 μm and not substantially more than 50% of said microaggregates being less than 0.2 μm, said agent stabilized with non-aggregated human serum albumin and buffer, said microaggregates being microaggregated at a pH of 4.5–9.5 but on the alkaline side of the apparent isoelectric point of said albumin.

32. An agent according to claim 31, said pH being between 5.4 and 7.0.

33. An agent according to claim 31, said agent comprising methylene diphosphonate and said pH being between 5.6 and 6.5.

34. A method for making an agent for labelling with Tc-99m for radioactive imaging, said method comprising microaggregating albumin in the presence of a reducing metal.

35. A method according to claim 34, said microaggregation being carried out in the presence of a stabilizing ligand for said reducing metal.

36. A method for making an agent for labelling with Tc-99m for radioactive imaging, said method comprising microaggregating human serum albumin in the presence of a stannous reducing metal, said microaggregation being carried out in the presence of a stabilizing ligand for said reducing metal selected from the group consisting of a phosphonate, a phosphate, an aminocarboxylate, a polyhydroxycarboxylate and a polycarboxylate.

37. A method according to claim 35, said microaggregation being carried out at a pH at which at least 90% of the microaggregates have a particle size not greater than 5 μm.

38. A method according to claim 37, said microaggregation being carried out at a pH at which not substantially more than 50% of the microaggregates have a particle size below 0.2 μm.

39. A method according to claim 37, said aggregation being carried out at a pH at which at least 40% have a particle size between 0.2 and 5 μm.

40. A method according to claim 37, said aggregation being carried out at a pH at which at least 40% of the microaggregates have a particle size between 0.2 and 3 μm.

41. A method according to claim 37, said aggregation being carried out at a pH at which at least the major portion of the microaggregates have a particle size between 0.2 and 3 μm.

42. A method according to claim 35, said aggregation being carried out at a pH between 4.5 and 9.5 but on the alkaline side of the apparent isoelectric point of said albumin.

43. A method according to claim 42, said pH being between 5.4 and 7.0.

44. A method according to claim 36, said ligand being a diphosphonate.

45. A method according to claim 36, said ligand being hydroxyethylene diphosphonate.

46. A method according to claim 36, said ligand being methylene diphosphonate.

47. A method according to claim 46, said microaggregates being carried out by heating at a pH of 5.4 to 6.6, at which at least 90% of the microaggregates have a particle size not greater than 5 μm and at least 40% have a particle size between 0.2 and 3 μm, said reducing metal being stannous and said albumin being human serum albumin.

48. A method according to claim 34, said microaggregation being carried out by passing a solution of undenatured human serum albumin and said reducing metal through a plurality of sequentially arranged heat exchangers in a semi-continuous manner.

49. A method according to claim 34, said reducing metal being stannous and said albumin being human serum albumin, said aggregation being carried out at a pH at which at least 90% of the microaggregates have a particle size not greater than 5 μm and not substantially more than 50% have a particle size below 0.2 μm.

50. A method according to claim 49, said microaggregation being carried out by heating at a pH between 4.5 and 9.5 but on the alkaline side of the apparent isoelectric point of said albumin at which at least the major portion of said microaggregates have a particle size between 0.2 μm and 3.0 μm.

51. A method according to claim 50, said pH being between 5.4 and 7.0.

52. A method according to claim 50, said pH being between 5.4 and 6.6

53. A method according to claim 34, said aggregation being carried out by heating albumin and said reducing metal by radiofrequency heating.

54. A method according to claim 34, said aggregation being carried out by heating albumin and said reducing metal by microwave heating.

55. A method according to claim 34, said aggregation being carried out by heating albumin and said reducing metal by induction heating.

56. A method of imaging the RES of a primate comprising injecting into the primate Tc-99m-labelled microaggregates of HSA and a reducing metal to concentrate said Tc-99m-labelled microaggregates in the RES.

57. A method according to claim 56, said composition containing a stabilizing ligand for said reducing metal.

58. A method for imaging the RES of a primate comprising injecting into the primate a composition comprising Tc-99m-labelled microaggregates of HSA and a stannous reducing metal to concentrate said Tc-99m-labelled microaggregates in the RES, said composition containing a diphosphonate stabilizing ligand for said reducing metal.

59. A method according to claim 58, at least 90% of said microaggregates having a particle size not greater than 5 μm and at least 40% have a particle size between 0.2 and 3 μm.

60. A preaggregated bulk, containing human serum albumin to be aggregated to microaggregates for radioactive labelling for use as an RES imaging agent, comprising a solution of unaggregated and undenatured human serum albumin, reducing metal and stabilizing ligand for said reducing metal, said bulk having a pH of between 4.5 and 9.5 but on the alkaline side of the isoelectric point of said albumin, the amount of ligand being sufficient to stabilize said stannous ions and prevent precipitation thereof before microaggregation but insufficient to provide any substantial non-RES target seeking properties when the microaggregates subsequently formed from said bulk are radioactively labelled and utilized for RES imaging.

61. A bulk according to claim 60, said pH being between 5.4 and 7.0.

62. A bulk according to claim 61, said reducing metal being stannous.

63. A preaggregated bulk containing human serum albumin to be aggregated to microaggregates for radioactive labelling for use as an RES imaging agent, comprising a solution of unaggregated and undenatured human serum albumin, stannous reducing metal and stabilizing ligand for said reducing metal, said bulk having a pH of between 5.6 and 6.5 but on the alkaline side of the isoelectric point of said albumin, the amount of ligand being sufficient to stabilize said stannous ions and prevent precipitation thereof before microaggregation but insufficient to provide any substantial non-RES target seeking properties when the microaggregates subsequently formed from said bulk are radioactively labelled and utilized for RES imaging, said ligand being a diphosphonate selected from the group consisting of methylene diphosphonate and hydroxyethylene diphosphonate.

64. A method for making an agent for labelling with Tc-99m for radioactive imaging, said method comprising microaggregating albumin in the presence of a reducing metal, at a pH between 3.5 and 9.5 but at a pH away from the apparent isoelectric point of said albumin.

65. A method according to claim 64 wherein said reducing metal is stannous and said albumin is human serum albumin, said step of microaggregating comprising heating said albumin and said reducing agent at said pH, thus forming microaggregates at least a major portion of which have a particle size between 0.2 μm and 5.0 μm, and at least 90% of which have a particle size not greater than 5.0 μm.

* * * * *

UNITED STATES PATENT AND TRADEMARK OFFICE
CERTIFICATE OF CORRECTION

PATENT NO. : 4,226,846
DATED : Oct. 7, 1980
INVENTOR(S) : Eugene L. Saklad

It is certified that error appears in the above-identified patent and that said Letters Patent are hereby corrected as shown below:

Column 2, line 16, change "stabilizng" to ---stabilizing---

Column 11, line 32, change "pertechnate" to ---pertechnetate---

Column 12, in table "1.6" should be moved from column entitled "organ" to column entitled --% of Injected Dose per Organ---

Column 17, line 22 change "isolectric" to ---isoelectric---
Column 17, line 24 change "isolectric" to ---isoelectric---
Column 17, line 40 change "know" to ---known---

Signed and Sealed this

Twelfth Day of May 1981

[SEAL]

*Attest:*

RENE D. TEGTMEYER

*Attesting Officer*  Acting Commissioner of Patents and Trademarks